US009465046B1

(12) United States Patent
Motzer et al.

(10) Patent No.: US 9,465,046 B1
(45) Date of Patent: Oct. 11, 2016

(54) INERTIAL SENSOR APPARATUS AND METHOD FOR CREATING AN NDI IMAGE WITH HAND SCANNING

(71) Applicant: The Boeing Company, Chicago, IL (US)

(72) Inventors: William Paul Motzer, Seattle, WA (US); Gary E. Georgeson, Tacoma, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 14/731,247

(22) Filed: Jun. 4, 2015

(51) Int. Cl.
| | |
|---|---|
| *G06K 9/40* | (2006.01) |
| *G06K 9/00* | (2006.01) |
| *G01P 15/02* | (2013.01) |
| *G06T 11/60* | (2006.01) |
| *G06T 5/00* | (2006.01) |
| *G01C 19/5698* | (2012.01) |

(52) U.S. Cl.
CPC ............ *G01P 15/02* (2013.01); *G01C 19/5698* (2013.01); *G06T 5/003* (2013.01); *G06T 11/60* (2013.01); *G06T 2207/10004* (2013.01)

(58) Field of Classification Search
CPC .. B64F 5/0018; B64F 5/0081; B64F 5/0045; G01N 21/8867; G01N 21/8422; G01N 21/8851; G01P 1/023; G01P 3/36; G01P 7/00; G01P 5/00; G01P 21/00

USPC ................. 382/141, 266, 274–275
See application file for complete search history.

(56) References Cited

U.S. PATENT DOCUMENTS

| | | | | |
|---|---|---|---|---|
| 5,097,350 | A | * 3/1992 | Baran | .................. G03G 15/221 358/401 |
| 5,549,803 | A | * 8/1996 | Schoess | ................. G01N 17/02 204/400 |
| 7,848,894 | B2 | 12/2010 | Motzer et al. | |
| 8,255,170 | B2 | 8/2012 | Kollgaard et al. | |
| 2008/0310754 | A1* | 12/2008 | Safai | ...................... G01B 15/04 382/275 |
| 2014/0208163 | A1* | 7/2014 | Domke | .............. G05B 23/0208 714/37 |

* cited by examiner

*Primary Examiner* — Kanjibhai Patel
(74) *Attorney, Agent, or Firm* — Baker & Hostetler LLP (57) ABSTRACT

A free-hand inspection apparatus for non-destructively inspecting a structure includes an array and an inertial sensor. The array includes a plurality of elements for transmitting and receiving inspection signals to/from a structure being inspected. The inertial sensor measures acceleration and angular rotation rate in three dimensions. A frame with a unique physical pattern on its edges, which are detectable by the system, is provided. In one embodiment, the frame comprises a special appliqué including a plastic sheet that has periodic edge features, or markings. The markings are detectable by the sensor and allow the system to correct the measurement distortions caused by the inertial sensors used for positioning while making scans. A computer-based process is provided to correct for drift when the sensor encounters one of these markings, thereby solving the problem of error accumulation and the resulting position inaccuracy.

13 Claims, 9 Drawing Sheets

INERTIAL SENSOR APPARATUS AND METHOD FOR CREATING AN NDI IMAGE WITH HAND SCANNING

TECHNICAL FIELD

The present disclosure relates generally to non-destructive inspection (NDI) systems, which are sometimes referred to as non-destructive evaluation (NDE) systems. These terms may be used interchangeably in the context of the present invention. More specifically, embodiments of the present disclosure relate to a free-hand inspection apparatus and system for non-destructively inspecting (or evaluating) a structure or surface.

BACKGROUND

An example of a non-destructive inspection apparatus is disclosed in U.S. Pat. No. 7,848,894, "Non-destructive Inspection Apparatus," Dec. 7, 2010, which is hereby incorporated by reference in its entirety. The disclosed NDI apparatus includes an inertial sensor and an array including a plurality of elements for transmitting and receiving inspection signals towards and from the structure being inspected. More specifically, the disclosed system employs an inertial sensor to determine position and orientation of an NDI sensor when doing non-destructive scanning of a surface or structure, e.g., the structure of an in-service aircraft.

Inertial sensors do not directly measure position and orientation. Instead, they sense acceleration and the angular rotation rate. Acceleration can be integrated to determine velocity. The velocity can then be integrated to determine position. The angular rotation rate can be integrated to determine orientation. The position and orientation values may be used to create an image of the structure under inspection using the measured NDI data. However, a problem with this approach is that, due to this double integration, uncertainties in position accumulate over time. The uncertain position information can distort the resulting image and render it unusable. A goal of the present invention is to provide a commercially feasible solution to this problem with NDI systems.

SUMMARY

Systems and methods in accordance with the present invention provide a solution to the integration drift problem that has emerged with NDI systems that employ inertial sensors. Inertial sensors can be implemented in the form of micro-electromechanical system (MEMS) accelerometer devices that measure direction, rotation, and acceleration. Integration drift is something that all inertial sensors suffer from, and it increases over time. As mentioned above, since inertial sensors directly measure acceleration and the acceleration measurements are integrated to determine the instantaneous velocity, small errors in the acceleration measurements cause larger errors to accumulate in the calculated velocity values.

One illustrative embodiment of the present invention employs a low-cost "frame" with a unique physical pattern on its edges, which are detectable by the NDI sensor. For example, in one embodiment, the frame comprises a special appliqué including a light-weight, inexpensive plastic sheet that has periodic edge features, or markings. An alternative embodiment employs opposing strips of tape each of which includes a similar pattern of edge markings. The edge markings are detectable by the sensor and allow the system to correct the measurement distortions caused by the inertial sensors used for positioning while making scans. A computer-based process is provided to correct for drift when the sensor encounters one of these markings. This solves the problem of error accumulation and the resulting position inaccuracy, provided that low-cost inertial sensors are sufficiently accurate between the periodic corrections. This solution enables effective use of inertial sensors for scanning applications.

Other aspects of the present invention are described below.

BRIEF DESCRIPTION OF THE DRAWINGS

FIGS. 1-3 are from U.S. Pat. No. 7,848,894.

DETAILED DESCRIPTION OF ILLUSTRATIVE EMBODIMENTS

The following detailed description is of the best currently contemplated modes of carrying out the disclosed invention. The description is not to be taken in a limiting sense, but is made for the purpose of illustrating the general principles of the disclosure. The scope of the disclosure, and the scope of protection, is best defined by the appended claims.

Illustrative embodiments of the invention will now be described in greater detail. First, we provide an overview, and then a more detailed description.

Overview

The present disclosure relates to an improvement to the invention described in U.S. Pat. No. 7,848,894. The improvement concerns a system for correcting distortions from the inertial sensors used for positioning while making scans. An illustrative embodiment employs a low-cost "frame" with a unique physical pattern on its edges, which are detectable by the NDI sensor. A computer-based process is provided to correct for drift, using one of these edge features that the sensor encounters. This solves the problem of error accumulation and the resulting position and rotation inaccuracy, provided that low-cost inertial sensors are sufficiently accurate between the periodic corrections. This solution enables effective use of inertial sensors for scanning applications.

Inertial sensor drift, which is especially problematic when using low-cost inertial sensors, means that an image of sufficient clarity is difficult to obtain with an NDI system such as described in U.S. Pat. No. 7,848,894. Other solutions to doing hand scanning of localized areas rely on stitching images together based on features in the image (but adequate features are often not present); using encoders that are attached to wheels that roll along the surface (slipping and tracking problems can be very problematic, and these encoders are mechanically fragile); and using instrumented rigid frames or tracks (which are often heavy, surprisingly expensive, and are often not very portable). The inventive solution described herein has advantages over these alternative solutions.

An embodiment of the invention described in U.S. Pat. No. 7,848,894 utilizes micromachined inertial sensors to record the position of NDI sensors as they are hand-scanned over an inspection surface. An issue with this approach is that, because of drift, the accuracy of the positioning of the inertial sensor is not usually sufficient to allow more than a small scan to be obtained. The present invention includes an apparatus and modification to the original position and orientation computation algorithm. It allows for practical implementation of hand-held NDI scanning by managing the position and orientation drift that is inherent in inertial position sensors. The invention may be implemented using a low-cost, disposable flexible plastic frame with unique physical patterns on the top and side that are detectable by the NDI sensor. These patterns allow the inertial position and orientation determination algorithm to periodically correct its position and orientation output, thereby minimizing sensor drift over the entire image and essentially confining it to one pass of the NDE sensor over the edge patterns where it is manageable such that an NDI image of useful size and sufficient clarity can be obtained. This frame has the additional benefit of allowing a picture of the "frame" on the inspection structure to be a reference as to where that NDI data was taken. In addition, this "picture" can be combined with a CAD description of the structure to register the NDI data with the structural CAD information. (Note that the drift measured after one pass can be corrected for, and not just re-set to zero, using a method as described in FIG. 12. In this method, we assume a constant drift by using a straight line, which is reasonable and simplest.)

Embodiments of the present invention are especially useful in the aviation industry since they can be used by airlines as an inexpensive portable NDI device that can be used by non-experts. The in-service aircraft industry has been waiting for a low-cost method to provide images of potential sub-surface damage. In addition, the inventive embodiments may be particularly advantageous for image-based Remote Expert NDI applications, since the invention enables uses of Remote Expert NDI in final assembly and in-service damage detection. This would allow rapid, low-cost disposition of some NDI inspections without calling trained NDI personnel to access the incident. Remote Expert NDI (see U.S. Pat. No. 8,255,170, "Remote Non-destructive Inspection Systems and Methods," Aug. 28, 2012) is a key capability being developed by aircraft manufacturers to address the need for having expert NDI personnel where airplanes need to be inspected.

Figure 1:
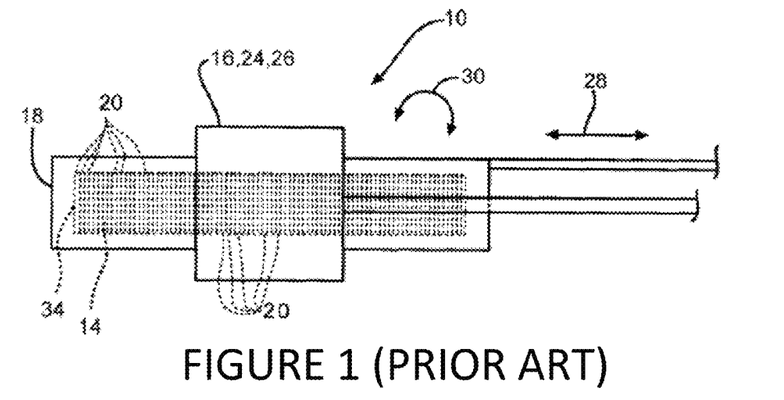
FIG. 1 illustrates a top view of an embodiment of a free hand inspection apparatus for non-destructively inspecting a structure.
Figure 2:
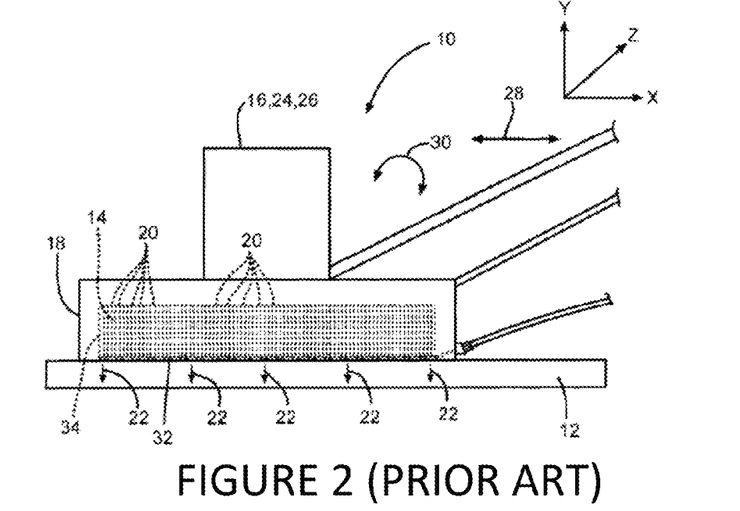
FIG. 2 illustrates a side view of the free-hand inspection apparatus of FIG. 1.
Figure 3:
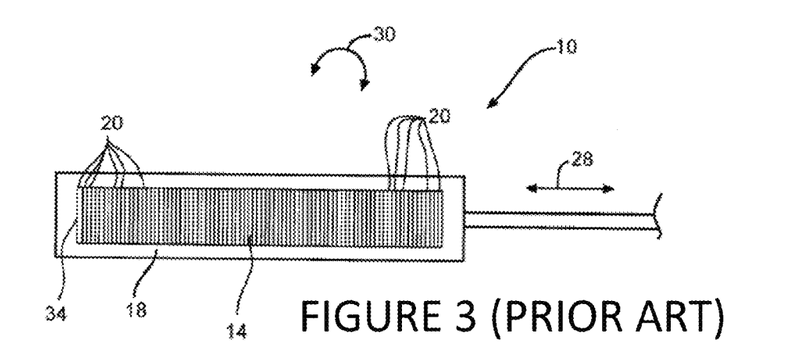
FIG. 3 illustrates a bottom view of the free-hand inspection apparatus.
Figure 5:
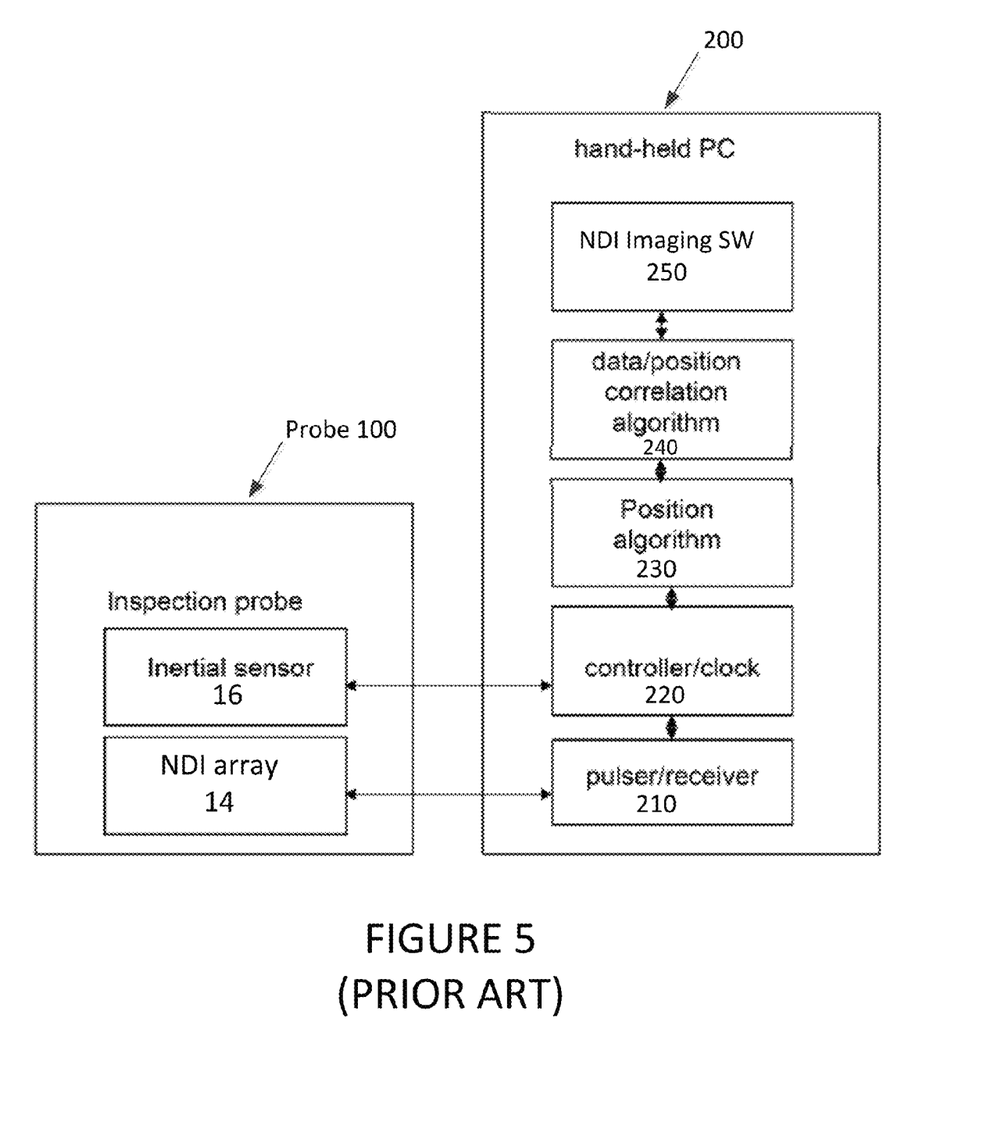
FIG. 5 illustrates certain key components of an illustrative embodiment of the system described by U.S. Pat. No. 7,848,894.
Figure 6:
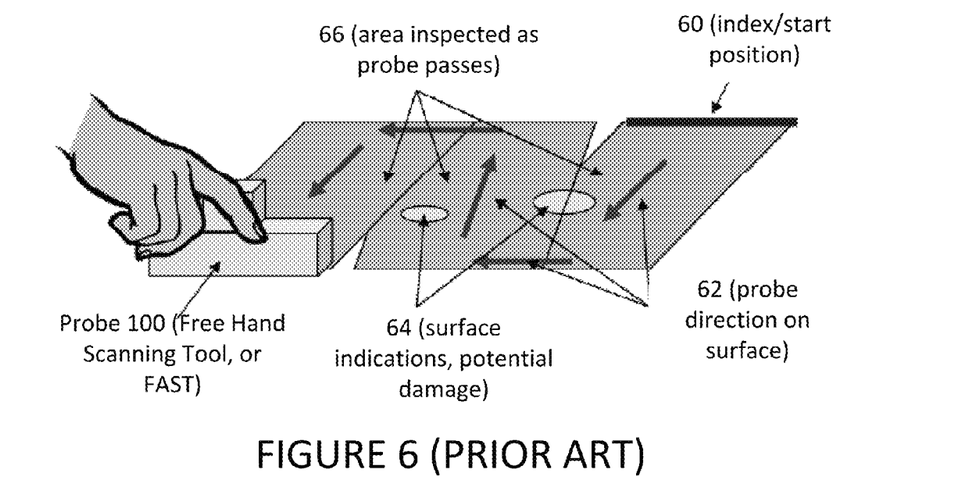
FIG. 6 illustrates how the FAST probe of FIG. 4 could be applied to a structure.

Detailed Description of Improved System for Performing Free-Hand NDI of a Surface The system of U.S. Pat. No. 7,848,894 uses input from a low-cost inertial sensor to calculate the position and orientation of the NDI sensor during data acquisition. This information is in turn used to produce an image of the inspection area using the ultrasonic data. FIGS. 1-3 are from U.S. Pat. No. 7,848,894, and FIGS. 4, 5, and 6 provide additional information to help explain the role that the inertial sensor and subsequent position determination plays in the NDI system.

FIGS. 1, 2, and 3 illustrate, top, side, and bottom views, respectively, of a free-hand inspection apparatus 10 for non-destructively inspecting a structure 12. The structure 12 may comprise an in-service aircraft, production aircraft, boat hull, automobile, pipe, building, bridge, or another type of structure that requires inspection. The structure 12 may comprise a linear structure, a three-dimensional curved structure, such as a partial cone or hemisphere, or other type of structure. As shown, the free-hand inspection apparatus 10 may comprise an array 14, an inertial sensor 16, and a bubble-shoe housing 18. The array 14 may comprise a plurality of elements 20 for transmitting and receiving inspection signals 22 towards and from the structure 12 being inspected. The array 14 may comprise a linear-array. The elements 20 may be adapted to transmit and receive inspection signals 22 comprising at least one of ultrasonic signals, eddy current signals, magnetic signals, and/or other types of inspection signals. The inertial sensor 16 may comprise a MEMS inertial sensor comprising an accelerometer 24 and a rate gyroscope 26.

The inertial sensor 16 may be adapted to measure acceleration 28 and angular rotation rate 30 in three dimensions (e.g., in X, Y, and Z directions of the array 14) using an array-centered coordinate system. The bubble-shoe housing 18 may be attached to the array 14 and be adapted to supply couplant 32 to the surface of the structure 12 being inspected. The array 14 may be disposed within a cavity 34 of the bubble-shoe housing 18. The inertial sensor 16 may be attached to the bubble-shoe housing 18. In other embodiments, one or more components of the free-hand inspection apparatus 10 may vary.

Figure 4:
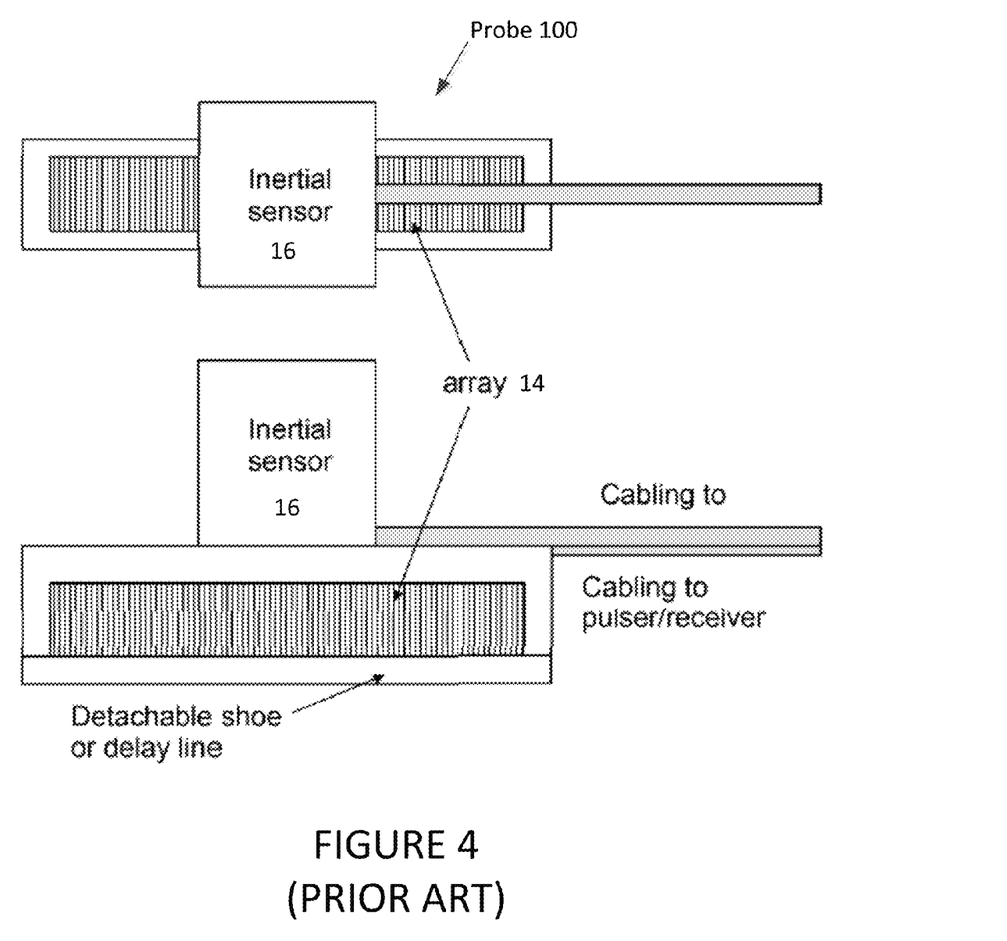
FIG. 4 illustrates a free-hand scanning tool (FAST) in which an ultrasonic array is used, although other NDI modalities such as eddy current or magnetic sensing could be employed as well.

Turning now to FIG. 4, as the operator moves the probe 100 over the surface under inspection, the results are "painted" onto the computer screen (not shown). The latest data to be collected at any particular position replaces the previous data at that location and is saved in computer memory and displayed on the computer screen. Post-scanning analysis of the data in the well-known A-, B-, and C-Scan formats can then be accomplished. The combination of the inertial MEMS devices and the array(s) allows NDI data to be taken very rapidly, in a wide brush-like swath, and in any orientation.

FIG. 5 illustrates key components of the system. As shown, a probe 100 includes an NDI array 14 and an inertial sensor 16. The probe 100 is coupled to a hand-held computer 200 as shown. The NDI array 14 is coupled to a pulser/receiver 210, and the inertial sensor 16 is coupled to a controller/clock 220. As shown, the computer 200 also includes a position algorithm 230, a data/position correlation algorithm 240, and imaging software 250.

Figure 7:
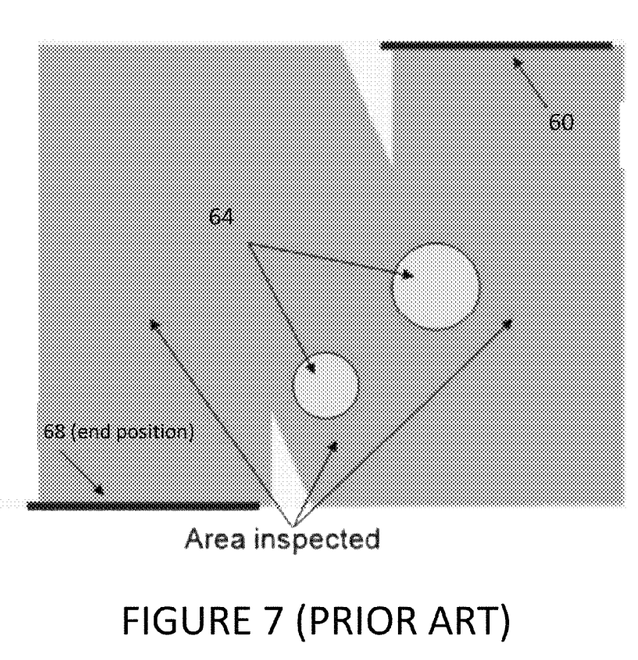
FIG. 7 illustrates a resultant NDI image.

FIG. 6 illustrates how the NDI data can be collected in brush-like motion. FIG. 7 shows what the data looks like in a C-scan format. If 3-D imaging software is used, the data taken from the scanner would allow spatial evaluation of a complex structure in 3-D space. As shown in FIG. 6, during a free hand scanning operation, the probe 100 is moved from a start position 60 along a path indicated by arrows 62, which represent the probe scanning direction on the surface being scanned. Surface indications 64, or areas of potential damage, are shown, and these are represented in the image data as depicted in FIG. 7. In the example of FIG. 6, three distinct areas 66 are inspected as the probe 100 is scanned along the paths shown. The scanning operation is complete once the probe 100 reaches the end position 68 (see FIG. 7).

A problem that has emerged with a practical implementation of the system described above with reference to FIGS. 1-7 is that the position of the NDI probe 100 cannot be accurately calculated for a long enough time period to make an image of useful size. Initial testing showed that the accuracy for one line of data would be sufficient but as multiple lines of scanning were done, the position methods become increasingly inaccurate. This is because of the method used to calculate the position of the NDI sensor from the inertial sensor measurements. Integration drift is something that all inertial sensors suffer from and it increases over time. Inertial sensors directly measure acceleration. These acceleration measurements are integrated to give the instantaneous velocity. Small errors in measuring the acceleration mean that there are errors in the velocity value calculated. As the instantaneous velocity is dependent on the previous velocity calculation, errors accumulate over time. This is further compounded in computing the instantaneous position as each position value is dependent on the calculated velocity value and the previous position values. This double integration to obtain position means that position errors accumulate in a manner roughly proportional to the time from the initial start position.

Therefore, a practical implementation was problematic without position values of greater accuracy and as presently proposed would result in an NDI image that was distorted and not optimal for quantitative disposition decisions for larger scan areas. An inventive solution to this problem leverages the ability of inertial systems to handle integration drift by periodically re-establishing a known position point. An illustrative embodiment of the present invention uses a light-weight, inexpensive plastic sheet or frame that can be rolled out and that has periodic markings that are detectable by the NDI sensor (typically an ultrasonic array). These selectable features can be used by the position computation algorithm to re-zero and re-orient the NDI sensor at the end of each scan swath. Alternatively, two strips of tape or plastic could be used to mark the edges of the scan area. This might be useful for odd scan areas. Although slightly less accurate, the known features in the tape and the fact that it is straight will be sufficient to give an adequate correction. This means that the drift in position caused by the double integration of the measured acceleration will not extend beyond one scan swath. Also, as both the beginning and ending positions and orientation are determined, the accuracy of the calculated positions between these two points can be improved.

Figure 8:
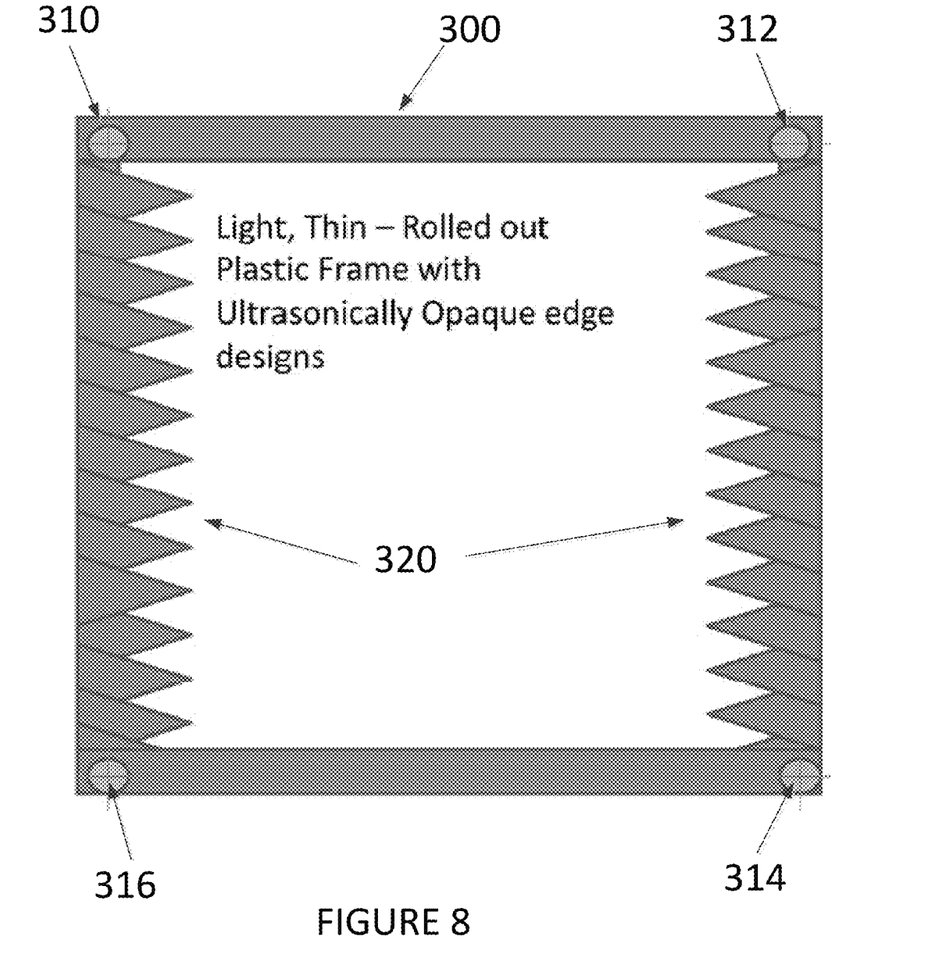
FIG. 8 illustrates a design of a plastic frame for correcting distortions from inertial sensors used for positioning while making scans.
Figure 9:
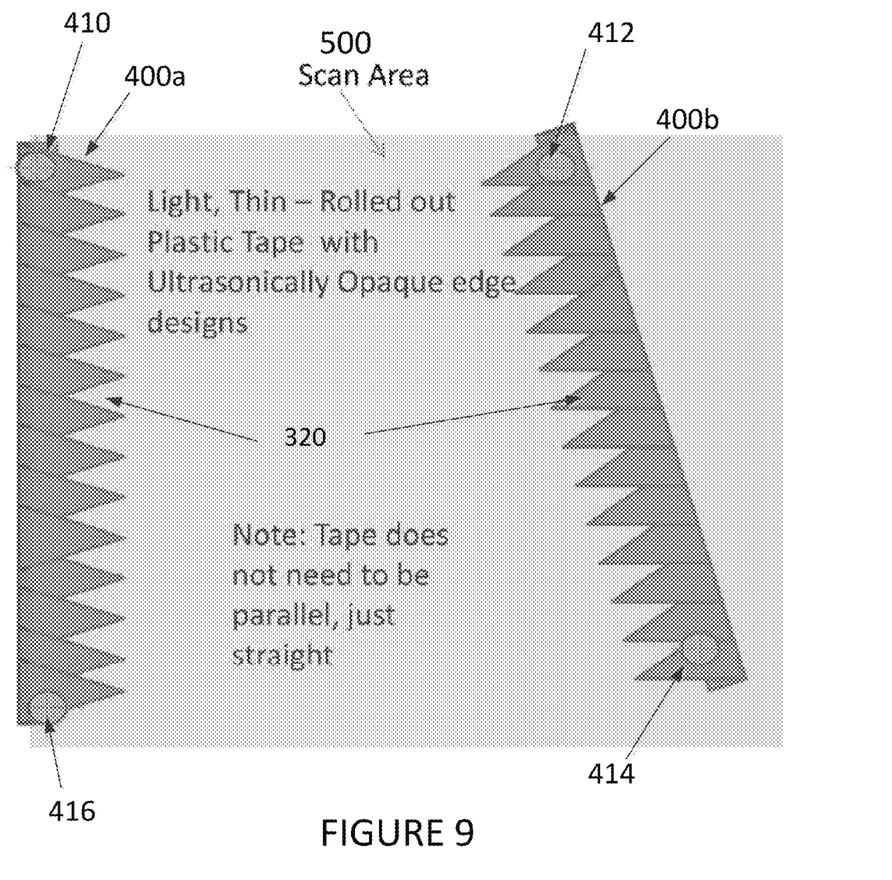
FIG. 9 illustrates a design of plastic edge tape for correcting distortions from inertial sensors used for positioning while making scans.
Figure 10:
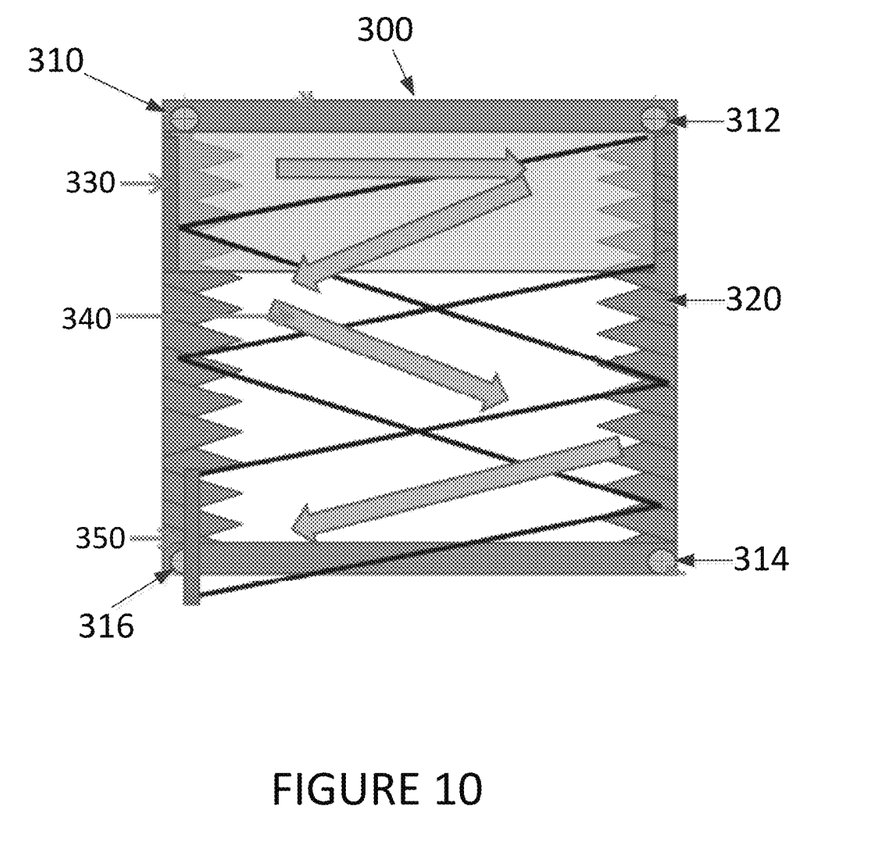
FIG. 10 illustrates a possible scan pattern using the plastic frame of FIG. 8.
Figure 11:
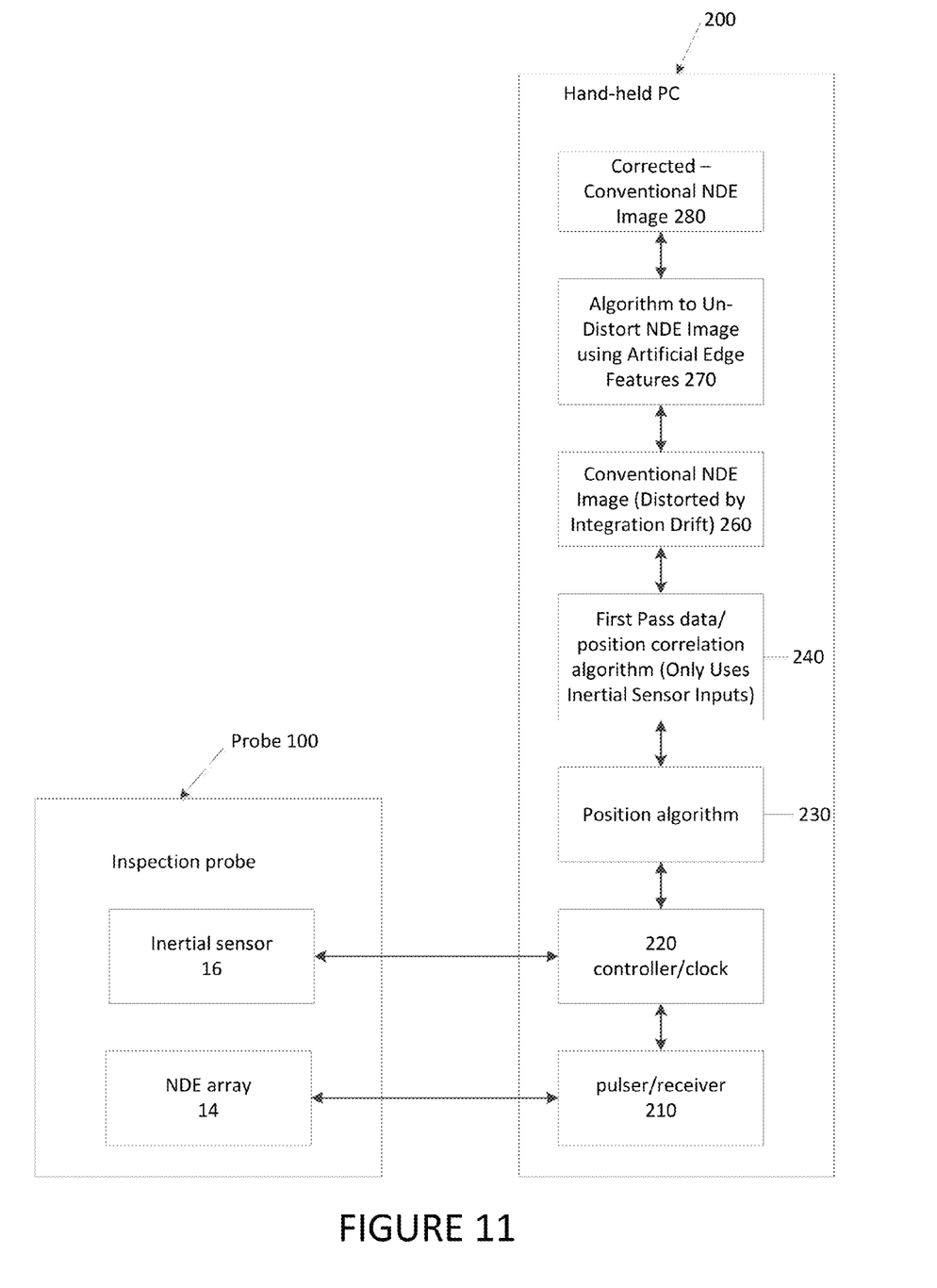
FIG. 11 illustrates certain key components of an illustrative embodiment of the present invention, including a new component for executing an algorithm to remove distortion from an NDI image using artificial edge features.

FIG. 8 shows the frame concept and FIG. 9 shows the tape concept. FIG. 10 illustrates scanning over the frame concept. FIG. 11 shows where this new invention will fit in the key components diagram.

Referring to FIG. 8, the frame 300 includes corner features 310, 312, 314, and 316, and edge features 320. The frame 300 may be made of Mylar™ (a form of polyester resin often used to make heat-resistant plastic films and sheets) or other material suitable for detection by the sensor array. For example, when using ultrasonic sensors, the frame is preferable made of an ultrasonically opaque material, i.e., so that ultrasonic signals will reflect off of the frame in a different way than they reflect from the surface under inspection. (Similarly, if eddy current sensors are used, the frame would preferably be made of a conductive material.) It would also be possible to use a conventional imaging sensor in conjunction with the NDI sensor to optically sense the tape pattern. Also, it may be advantageous to use a suitable adhesive to adhere the frame 300 to the surface under inspection. Alternatively, static cling may also be used to adhere the appliqué to the surface under inspection.

FIG. 9 depicts an embodiment in which a light, thin plastic tape with ultrasonically opaque edge designs is employed instead of the frame structure of FIG. 8. As shown, two strips 400a and 400b of such tape are disposed on opposing sides of a scan area 500. It is not necessary for the tape strips to be parallel, although it is necessary for each strip to be straight, which can easily be done by stretching the tape out prior to and during its application.

In the context of the illustrative embodiments of FIGS. 8 and 9, the edge designs 320 (FIG. 8) or 400a and 400b (FIG. 9), have a known and computationally-detectable geometry and orientation. This aspect of the edge design is important since it enables the image correction software (element 270 in FIG. 11) to easily correct the detected edge image (e.g., by rotation and translation of the image to correct for inertial sensor drift) and to make similar corrections of the scan image. Other edge designs are possible including ones with a similar repeating pattern that repeats over a period that is larger than the sensor width. This may be advantageous in some applications for image re-construction. Also, corner features 310, 312, 314, and 316 (FIG. 8) or 410, 412, 414, and 416 (FIG. 9) are provided. These features can be used to locate the scan area in the overall geometry of the surface being inspected. For example, if the surface is the surface of an aircraft, the corner features 410, 412, 414, and 416 could be correlated to specific rivet locations, or even to a defined area beneath a certain window in the fuselage or even by other more sophisticate metrological means such as a laser position system or laser tracker.

FIG. 10 illustrates use of the frame 300 for hand-scanning of a surface. The frame 300 comprises a light, thin rolled out plastic frame with ultrasonically opaque edge feature. Precise corner points 310, 312, 314, and 316 may be included for scan registration (if used). The transducer array start point 330, scan direction 340, and stop point 350 are indicated as well.

FIG. 11, which is similar to FIG. 5, illustrates key components of the improved system. As shown, the probe 100 includes an NDI array 14 and an inertial sensor 16, and the probe 100 is coupled to a hand-held computer 200'. The NDI array may comprise an array of ultrasonic transducers for detecting defects in the surface being inspected. Other types of inspection sensors that may be employed include eddy current sensors and optical sensors. If eddy current sensors are used, then the frame or tape would preferably be made of a conductive material. If optical sensors are used, the frame or tape would preferably be made of a visually distinct material. As in the prior system, the NDI array 14 is coupled to a pulser/receiver 210, and the inertial sensor 16 is coupled to a controller/clock 220. In the improved system, the computer 200' is new and different from the computer 200 of the prior system. The new computer 200' includes a position algorithm 230, a new data/position correlation algorithm 240', and different imaging software. In the new computer 200', the NDI imaging software 250 of the FIG. 5 system has been replaced by elements 260, 270, and 280.

Figure 12:
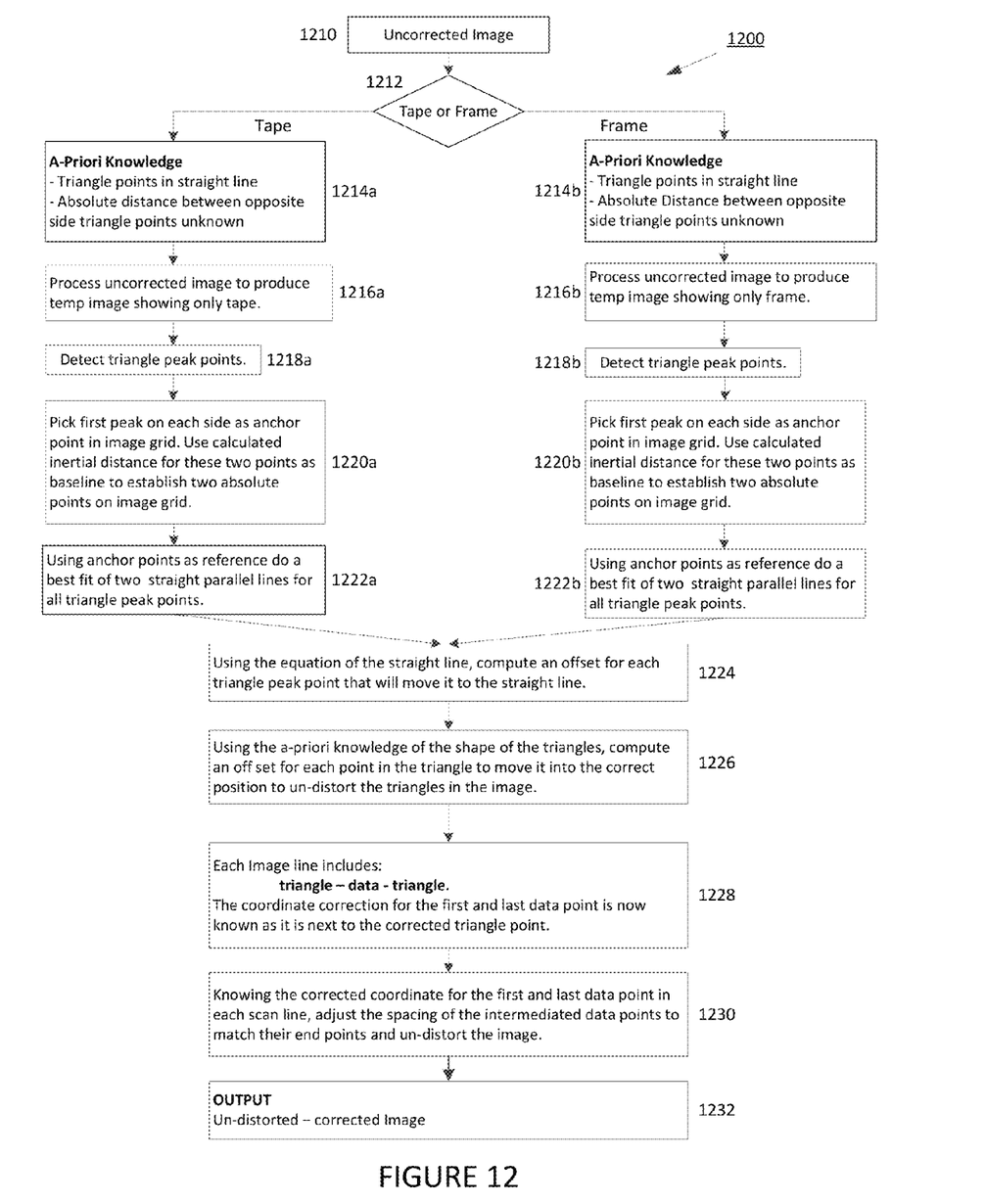
FIG. 12 is a flowchart of an image correction process in accordance with an embodiment of the present invention.

FIG. 12 is one example of a process 1200 that could be used to correct an image 1210 distorted by integration drift.

The process 1200 uses the outline of the triangles and the known geometrical description of them and their possible placements to un-distort the initial image 1210. As shown, the process includes the following step-by-step process:

In step 1212, we determine whether tape or frame structure is used to define edge features. If tape, proceed to steps 1214a-1222a. If frame, proceed to steps 1214b-1222b.

In both steps 1214a and 1214b, we assume a priori that the triangle points lie in a straight line. Also, we assume that the absolute distance between opposite side triangle points is unknown for tape but known for frame.

In steps 1216a and 1216b, the uncorrected image 1210 is processed to produce a temporary image showing only the tape or frame.

In steps 1218a and 1218b, the triangle peak points are detected.

In steps 1220a and 1220b, the first peak on each side is selected as an anchor point in the image grid. The calculated inertial distance for these two points is used as a baseline to establish two absolute points on the image grid for the tape, while the known distance is used for the frame.

In steps 1222a and 1222b, a best fit of two straight parallel lines for all triangle peak points is determined using the anchor points as a reference.

In step 1224, we use the equation of the straight line to compute an offset for each triangle peak point that will move it to the straight line.

In step 1226, we use the a priori knowledge of the shape of the triangles to compute an offset for each point in the triangle to move it into the correct position to un-distort the triangles in the image.

Block 1228 indicates that each image line includes information in the form of triangle-data-triangle. The coordinate correction for the first and last data point is now known as it is next to the corrected triangle point.

In step 1230, using the known corrected coordinate for the first and last data point in each scan line, the spacing of the intermediated data points is adjusted to match their end points and un-distort the image.

In step 1232, the un-distorted, corrected image is output as indicated.

CONCLUSION

Systems and methods are disclosed in accordance with one or more embodiments of the invention to provide NDI services. For example, NDI testing, remote evaluation, and repair decision making for aircraft line maintenance may be provided in accordance with some embodiments. The techniques disclosed herein may provide certain advantages with respect to evaluation and repair decisions that may be made from any location remote from the inspection scene and in time to decide whether to dispatch an aircraft with minimal delay, make a quick temporary repair, or remove it from service for more extensive repair. This may provide significant cost savings when it is determined that a flight can be safely dispatched, rather than cancelled due to a lack of valid inspection data that may lead to an unnecessarily conservative decision on flight worthiness.

Embodiments described above illustrate but do not limit the invention. It should also be understood that numerous modifications and variations are possible in accordance with the principles of the invention. For example, although the embodiments are described with reference to aircraft, including but not limited to composite aircraft structures, one will readily appreciate that the systems and methods described herein may be applicable to any inspection object, including many other structures, materials, and systems. Examples may include, but are not limited to, marine vessels (e.g., in transit or at port), spacecraft, rail transportation vehicles, ground vehicles, automobiles, and fixed standing structures, such as buildings, bridges, tunnels, and the like. Accordingly, the scope of the invention is defined only by the following claims.

We claim:

1. A system for performing free-hand non-destructive inspection (NDI) of a surface, comprising:
    a probe comprising an array of sensor elements for transmitting and receiving inspection signals towards and from a surface under inspection, and an inertial sensor for measuring acceleration and angular rotation of the array;
    an appliqué comprising edge markings detectable by the array of sensor elements; and
    a computer operatively coupled to the probe, wherein the computer is configured to receive signals from the array of sensor elements and the inertial sensor and to generate an NDI image of the surface, and wherein the computer includes a software-based process for removing distortions in the NDI image using image data corresponding to the edge markings, wherein the software-based process for removing distortions in the NDI image comprises:
        processing an uncorrected image to produce a temporary image showing the edge markings;
        detecting peak points in the temporary image;
        selecting a first peak on each side of the temporary image as an anchor point in an image grid, and using a calculated inertial distance for these two points as a baseline to establish two absolute points on the image grid;
        determining a best fit of two straight parallel lines for all peak points using the anchor points as a reference;
        computing an offset for each peak point that will move each peak point to the straight line;
        computing an offset for each of a plurality of points to move the point into the correct position to un-distort the image points corresponding to the edge markings;
        determining a coordinate correction for a plurality of image data points; and
        using a corrected coordinate for a first and last data point in each scan line, adjusting the spacing of intermediated data points to match the end points of the intermediated data points and un-distort the image.

2. The system recited in claim 1, wherein the array comprises a plurality of ultrasonic sensor elements and the appliqué comprises ultrasonically opaque edge features.

3. A system for performing free-hand non-destructive inspection (NDI) of a surface, comprising:
    a probe comprising an array of sensor elements for transmitting and receiving inspection signals towards and from a surface under inspection, and an inertial sensor for measuring acceleration and angular rotation of the array;
    an appliqué comprising edge markings detectable by the array of sensor elements; and
    a computer operatively coupled to the probe, wherein the computer is configured to receive signals from the array of sensor elements and the inertial sensor and to generate an NDI image of the surface, and wherein the computer includes a software-based process for removing distortions in the NDI image using image data corresponding to the edge markings;

wherein the process for removing distortions in the NDI image uses an outline of the edge markings and a known geometrical description of the edge markings and the possible placements of the edge markings to remove distortions in the NDI image.

4. The system recited in claim 3, wherein the edge markings include triangles disposed along two opposing lines on the surface using the appliqué, wherein each triangle includes a peak point that lies on a substantially straight line.

5. The system recited in claim 4, wherein the process for removing distortions in the NDI image comprises:

processing the uncorrected image to produce a temporary image showing only the appliqué;

detecting triangle peak points in the temporary image;

selecting a first peak point on each side of the image as an anchor point in an image grid, and using a calculated inertial distance for these two points as a baseline to establish two absolute points on the image grid if tape is used and using the known distance if a frame is used;

computing a best fit of two straight lines for all triangle peak points using the anchor points as a reference if tape is used and computing a best fit of two parallel straight lines for all triangle peak points using the anchor points as a reference if frame is used;

computing an offset for each triangle peak point that will move each triangle peak point to the straight line;

computing an offset for each point in the triangle to move each point into the correct position to un-distort the triangles in the image;

determining a coordinate correction for a plurality of image data points; and using a corrected coordinate for a first and last data point in each scan line, adjusting the spacing of intermediated data points to match the end points of the inter-mediated data points and un-distort the image.

6. In a system for performing free-hand non-destructive inspection (NDI) of a surface, a computer-based process for removing distortions in an image using image data corresponding to edge markings, wherein the process uses an outline of the edge markings and a known geometrical description of the edge markings and the possible placements of the edge markings to remove distortions in the image, comprising:

processing an uncorrected image to produce a temporary image showing the edge markings;

detecting peak points in the temporary image;

selecting a first peak on each side of the temporary image as an anchor point in an image grid, and using a calculated inertial distance for these two points as a baseline to establish two absolute points on the image grid;

determining a best fit of two straight parallel lines for all peak points using the anchor points as a reference;

computing an offset for each peak point that will move each peak point to the straight line;

computing an offset for each of a plurality of points to move the point into the correct position to un-distort the image points corresponding to the edge markings;

determining a coordinate correction for a plurality of image data points; and using a corrected coordinate for a first and last data point in each scan line, adjusting the spacing of intermediated data points to match the end points of the inter-mediated data points and un-distort the image.

7. The process recited in claim 6, wherein the edge markings include triangles disposed along two opposing lines on the surface using an appliqué, wherein each triangle includes a triangle peak point that lies on a substantially straight line.

8. The process recited in claim 7, wherein the appliqué is used to provide the edge markings and wherein the edge markings are detectable by an array of sensor elements.

9. The process recited in claim 8, wherein the array of sensor elements transmit and receive inspection signals towards and from the surface on which the appliqué is disposed, and an inertial sensor is used to measure acceleration and angular rotation of the array.

10. The process recited in claim 9, wherein the array comprises a plurality of ultrasonic sensor elements and the appliqué comprises ultrasonically opaque edge features.

11. The process recited in claim 9, wherein the appliqué comprises a plastic frame adhered to the surface.

12. The process recited in claim 9, wherein the appliqué comprises tape applied to the surface.

13. The process recited in claim 9, wherein the appliqué comprises an adhesive portion using static cling to adhere the appliqué to the surface.

* * * * *